(12) United States Patent
Crnkovich et al.

(10) Patent No.: US 9,731,059 B2
(45) Date of Patent: Aug. 15, 2017

(54) SENSOR AND METHOD OF SENSING FOR DIALYSIS MACHINE

(71) Applicant: Fresenius Medical Care Holdings, Inc., Waltham, MA (US)

(72) Inventors: Martin Crnkovich, Walnut Creek, CA (US); Aiyuan Wang, San Ramon, CA (US); Fei Wang, Concord, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 506 days.

(21) Appl. No.: 13/933,828

(22) Filed: Jul. 2, 2013

(65) Prior Publication Data

US 2015/0008183 A1  Jan. 8, 2015

(51) Int. Cl.
*B01D 61/24* (2006.01)
*A61M 1/16* (2006.01)
(Continued)

(52) U.S. Cl.
CPC ........ *A61M 1/1601* (2014.02); *A61M 1/1605* (2014.02); *A61M 1/1607* (2014.02);
(Continued)

(58) Field of Classification Search
CPC .... A61M 1/16; A61M 1/1601; A61M 1/1605; A61M 1/1607; A61M 1/1609;
(Continued)

(56) References Cited

U.S. PATENT DOCUMENTS

| 4,399,036 A * | 8/1983 | Babb | A61M 1/1656 |
| | | | 210/321.71 |
| 5,015,389 A | 5/1991 | Portillo, Jr. | |

(Continued)

FOREIGN PATENT DOCUMENTS

| EP | 0 846 470 A1 | 6/1998 |
| WO | WO 96/25214 A1 | 8/1996 |
| WO | WO 2010/024963 A1 | 3/2010 |

OTHER PUBLICATIONS

International Patent Application No. PCT/US2014/045215, Search Report (Nov. 5, 2014).

*Primary Examiner* — Joseph Drodge
(74) *Attorney, Agent, or Firm* — Leydig, Voit & Mayer, Ltd.

(57) ABSTRACT

A dialysis machine useful in hemodialysis can process or treat a reverse osmosis water flow received through the machine to prepare a dialysate. The machine can include an additive source to introduce an additive, such as bicarbonate, to the reverse osmosis water flow. The machine can include a sensor in fluid communication with the additive introduction point that can measure the conductivity or similar characteristic of the solution. During a first time period when additive is actively introduced to the reverse osmosis water flow, the sensor can measure a relatively high conductivity value. During a second time period when additive is not introduced to the reverse osmosis water flow, the sensor can measure a relatively low conductivity value. The dialysis machine can include a controller that processes these measurements to assist control and operation of the machine.

20 Claims, 4 Drawing Sheets

(51) Int. Cl.
  *C02F 1/44*   (2006.01)
  *C02F 1/00*   (2006.01)
  *C02F 103/02*    (2006.01)
  *C02F 1/68*      (2006.01)

(52) U.S. Cl.
  CPC ......... *A61M 1/1656* (2013.01); *B01D 61/243* (2013.01); *C02F 1/008* (2013.01); *A61M 2205/3317* (2013.01); *C02F 1/44* (2013.01); *C02F 1/441* (2013.01); *C02F 1/68* (2013.01); *C02F 2103/026* (2013.01); *C02F 2209/05* (2013.01)

(58) Field of Classification Search
  CPC ..... A61M 1/1656; B01D 61/30; B01D 61/32; C02F 1/008; C02F 1/44; C02F 1/441; C02F 1/68
  USPC ........ 210/93, 96.2, 138, 139, 140, 143, 639, 210/646, 647, 652, 746; 324/439
  See application file for complete search history.

(56) References Cited

U.S. PATENT DOCUMENTS

| | | | |
|---|---|---|---|
| 5,157,332 A | 10/1992 | Reese | |
| 5,498,338 A | 3/1996 | Kruger et al. | |
| 5,716,531 A * | 2/1998 | Kenley | A61L 2/04 210/645 |
| 5,744,031 A * | 4/1998 | Bene | A61M 1/16 210/143 |
| 5,972,223 A * | 10/1999 | Jonsson et al. | A61L 2/0023 137/88 |
| 5,997,745 A | 12/1999 | Tonelli et al. | |
| 6,120,689 A | 9/2000 | Tonelli et al. | |
| 6,156,002 A * | 12/2000 | Polaschegg | A61M 1/16 210/646 |
| 6,607,697 B1 * | 8/2003 | Muller | A61M 1/1656 210/257.2 |
| 2003/0010701 A1 * | 1/2003 | Collins | A61M 1/3413 210/321.6 |
| 2006/0054215 A1 * | 3/2006 | Remkes | A61M 1/16 137/107 |
| 2008/0000835 A1 * | 1/2008 | Rogers | A61K 31/19 210/647 |
| 2009/0173682 A1 * | 7/2009 | Robinson | A61M 1/16 210/232 |
| 2010/0051552 A1 * | 3/2010 | Rohde | A61M 1/1656 210/647 |
| 2010/0326916 A1 | 12/2010 | Wrazel et al. | |
| 2011/0189048 A1 | 8/2011 | Curtis et al. | |
| 2011/0192796 A1 | 8/2011 | Smejtek et al. | |
| 2011/0300231 A1 | 12/2011 | Peterson et al. | |
| 2012/0068723 A1 | 3/2012 | Sullivan | |
| 2013/0056419 A1 * | 3/2013 | Curtis | A61M 1/1656 210/647 |
| 2013/0113350 A1 * | 5/2013 | Lee | A47G 1/12 312/224 |
| 2013/0116650 A1 * | 5/2013 | Vantard | A61M 1/1656 604/506 |
| 2014/0190886 A1 * | 7/2014 | Pudil | A61M 1/1696 210/632 |
| 2014/0199193 A1 * | 7/2014 | Wilt | A61M 1/1037 417/477.2 |

* cited by examiner

SENSOR AND METHOD OF SENSING FOR DIALYSIS MACHINE

BACKGROUND OF THE INVENTION

Hemodialysis is performed to treat patients suffering from renal failure, kidney problems or other related conditions in which the kidneys are unable to adequately remove impurities and waste products from the patient's blood. In the hemodialysis process, a typical dialysis machine removes the blood from the patient's body and directs it through a filtration device referred to as a dialyzer that filters the cleaned blood for return to the patient. The filtration process is performed by directing a solution, often referred to as a dialysate, through the dialyzer, and which is separated from the blood therein by a membrane so that waste products are drawn or diffuse into the dialysate. To facilitate treatment of different patients with different conditions, the dialysate is sometimes prepared in part onsite by or with the assistance of the dialysis machine. For example, various additives may be introduced to the solution to adjust the treatment for patient-specific characteristics such as, for example, bicarbonate to reduce acidity of the blood being treated.

To assist in onsite preparation of the dialysate, various sensors and controls are incorporated into the dialysis machine to monitor the preparation process. Using these sensors and controls, the dialysis machine can be designed to automatically make adjustments during the dialysis treatment, or a health technician monitoring the sensors and controls can make the necessary adjustments. The sensors and controls may therefore play a significant role during the dialysis treatment. The present disclosure is directed to supplementing and improving the operation and functionality of the sensors and controls associated with a dialysis machine.

BRIEF SUMMARY OF THE INVENTION

The disclosure describes a dialysis machine adapted to prepare dialysate from a purified reverse osmosis water source. The dialysis machine can introduce additives, such as bicarbonate, to the reverse osmosis water flow through the machine to adjust the characteristics of the dialysate in accordance with the dialysis treatment provided. The dialysis machine can include a sensor downstream of the additive introduction point that receives or encounters the reverse osmosis water flow. The sensor can be designed to sense the conductivity or another characteristic of the solution encountered downstream of the additive introduction point.

In an embodiment, the introduction of the additive may occur intermittently, such as according to a predetermined schedule, or selectively based on operating conditions of the machine, treatment conditions or intervention by a technician. Accordingly, the sensor may measure a relatively high conductivity value or a similar measureable characteristic during a first time period when additive is introduced to the reverse osmosis water flow and may measure a relatively low conductivity value or similar change in another characteristic during a second time period when additive is not introduced to the stream. The measured low conductivity value can be associated with pure reverse osmosis water, which ideally should approach zero conductivity.

A computerized or electronic controller associated with the dialysis machine can be programmed with executable software instructions that process the measured high and low conductivity values to assist operation of the dialysis machine. For example, the controller can initiate protective measures if it determines the reverse osmosis water is unacceptable for performing the dialysis treatment. The controller can also process the measurements to determine the amount of additive introduced to the reverse osmosis water flow.

A possible advantage of the disclosure is that the same sensor can be used to monitor two different operating conditions of the dialysis machine. A related potential advantage is that the conductivity values or a comparable characteristic measured by the sensor can assist in controlled operation and adjustment of the dialysis machine. These and other advantages will become apparent from the following detailed description and the accompanying drawings.

DETAILED DESCRIPTION OF THE INVENTION

Figure 1:
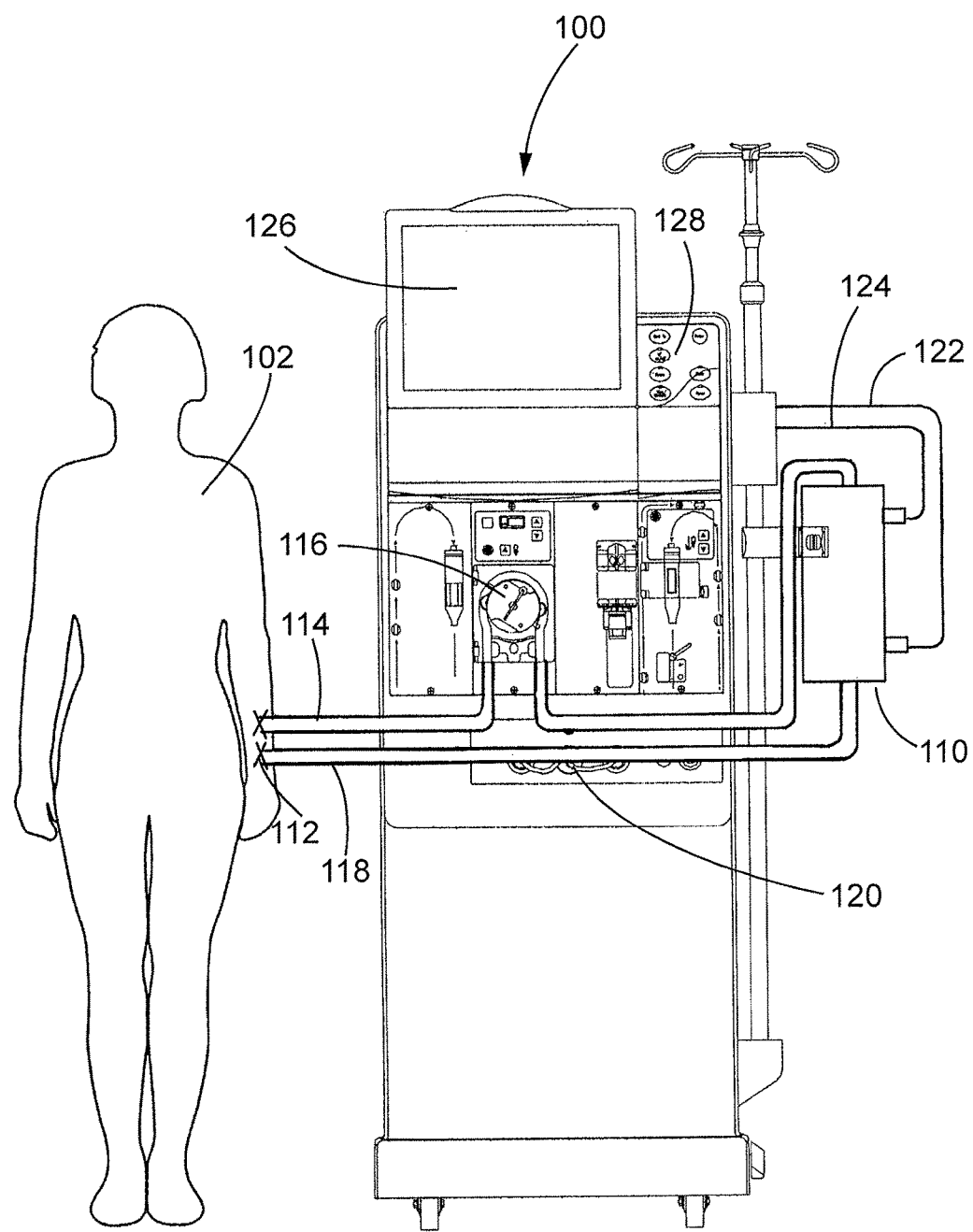
FIG. 1 is a front elevational view of a hemodialysis machine for treating blood removed from a patient and to assist in the onsite preparation of a dialysate.

Now referring to the drawings, wherein like reference numbers refer to like elements, there is illustrated in FIG. 1 a dialysis machine 100 performing a hemodialysis treatment on a patient 102. It should be noted that although various aspects of the present disclosure are described with respect to hemodialysis treatment, these aspects may have application beyond hemodialysis treatment and are not intended to be specifically limited to hemodialysis, nor are the claims so limited unless explicitly stated. The dialysis machine 100 can be equipped with a dialyzer 110 in which the filtration of blood is performed. The dialyzer 110 can be a cross-flow dialyzer in which blood flowing in one direction is separated from a dialysate fluid flowing in the opposite direction by a semi-permeable membrane. During the dialysis process, solutes and impurities in the blood can transfer across the membrane to the dialysate to be directed out of the dialyzer 110. In various embodiments, the dialyzer 110 may be a single use device or may be configured for multiple uses.

To direct blood from the patient 102 to the dialyzer 110, a catheter 112 inserted into the patient and can be connected to the dialysis machine 100 via tubing or a removal line 114. To maintain the flow of blood from the patient 102 to the dialyzer 110, a pump 116 such as a rotary peristaltic pump can be disposed along the removal line 114 and applies a pressure to the lines that directs or supplements blood flow in the appropriate direction. Filtered blood from the dialyzer 110 is returned to the patient 102 via a return line 118.

To supply the fresh dialysate to the dialyzer 110, the dialysis machine 100 can include a dialysis system 120 that connects to the dialyzer via a dialysate supply line 122. The spent or contaminated dialysate can be returned from the dialyzer via a dialysate return line 124 for storage in a suitable receptacle and eventual disposal. The dialysis supply line 122 and dialysate return line 124 can be releasably coupled to the dialysis machine 100. The dialysis machine 100 can be configured to monitor and control the dialysate system 120 to make real-time adjustments to the dialysis treatment. To facilitate these adjustments, the dialysis machine 100 can include a display device 126, such as a liquid crystal display or touch screen, and a control panel 128 including a key pad, to display information about the dialysis treatment and to interface with an operator or technician. In the illustrated embodiment, the dialysis machine 100 can be configured as a piece of equipment for portable installation at a hospital or other treatment facility, but in other embodiments can be designed as a smaller, mobile unit intended for at-home use.

Figure 2:
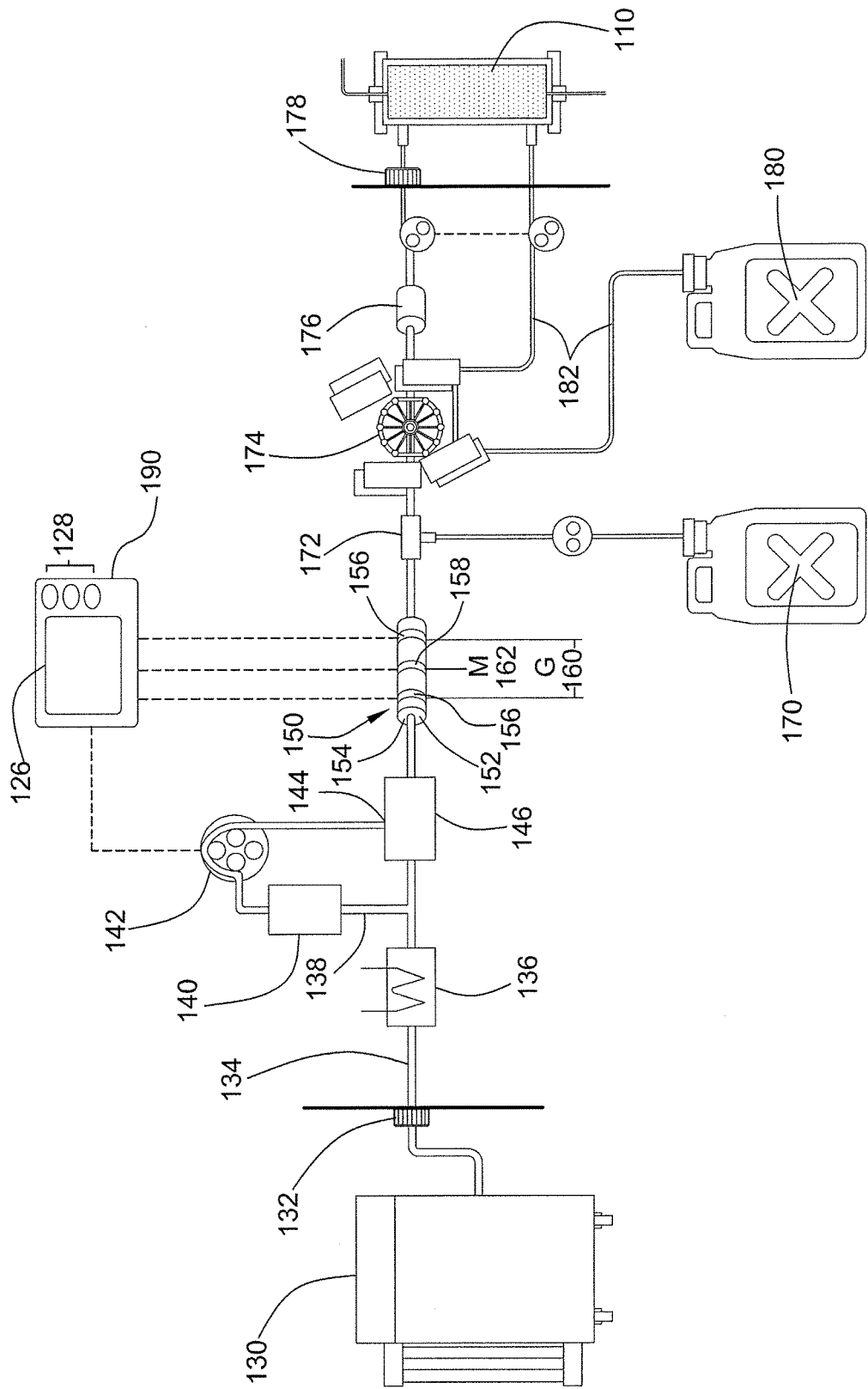
FIG. 2 is a schematic of the components of the hemodialysis machine, including a controller and sensors, for preparing the dialysate from a reverse osmosis water source.

Referring to FIG. 2, the dialysate system 120 including various internal components of the dialysis machine 100 are shown in a schematic representation arranged and interconnected together and to the dialyzer 110, although in other embodiments, other arrangements are contemplated. The dialysate preparation process typically begins with introducing a reverse osmosis water flow from a reverse osmosis water source 130 in fluid communication with the dialysis machine 100. The reverse osmosis water source 130 produces or provides reverse osmosis quality water for converting into dialysate, which may have a low sodium concentration and is non-ionic. The reverse osmosis water source 130 may include several filters and similar devices for purifying and de-ionizing less pure water to the required levels. To direct the reverse osmosis water flow to the dialysis machine 100, the reverse osmosis water source 130 is coupled to a reverse osmosis water inlet port 132 disposed on the machine via hoses, tubing or the like. Pumps in either or both the reverse osmosis water source 130 or in the dialysis machine 100 can provide selectively adjustable fluid pressure to direct and regulate the reverse osmosis water intake.

To direct the introduced reverse osmosis water flow through the dialysis machine, suitable medical grade piping, hoses and/or tubing 134 is disposed throughout the machine, interconnecting the internal components. The tubing 134 thereby delineates a channel or flow path of the reverse osmosis water through the dialysis machine 100 to the dialyzer 110. To elevate the temperature of the reverse osmosis water flow to a temperature suitable for interfacing with the extracorporeal blood in the dialyzer 110, the tubes 134 can direct the reverse osmosis water flow through a heater 136.

As discussed above, to prepare the dialysate for the treatment process, the dialysate system 120 can introduce various additives to the reverse osmosis water flow. For example, to introduce an additive such as bicarbonate, the tubing 134 can form a branch 138 to divert a portion of the reverse osmosis water flow to a reservoir or additive source 140. The additive source 140 can be a container such as a plastic bag disposed along and in fluid communication with the branch 138 that may store dried bicarbonate concentrate. The portion of the reverse osmosis water flow directed to the additive source can mix with the bicarbonate concentrate to create a bicarbonate solution. In the described embodiment, the plastic bag may be discarded and replaced after each treatment. In other embodiments, the additive source can be a large reservoir that can be periodically replenished during the course of multiple treatments. Furthermore, the additive can be provided as a premixed fluid solution.

To selectively and measurably introduce the bicarbonate solution to the undiverted portion of the reverse osmosis water flow, an additive pump 142 can be disposed along the branch 138 downstream of the additive source 140, though in other embodiments, the additive pump may be upstream of the source. To precisely mange the amount or volume of additive introduced to the main portion of the reverse osmosis water flow, the additive pump 142 can be a metering pump such as one driven by a stepper motor or an adjustable linear actuator. The fluid channels through the additive pump 142 may be hermetically sealed from the other components to preserve the purity of the solution. The bicarbonate solution can be introduced to the main flow of the reverse osmosis water flow at an additive introduction point 144 in fluid communication with the main branch of the tubing. To adequately mix the bicarbonate solution with the reverse osmosis water flow, a mixing chamber 146 can be disposed along the tubing 134 at, for example, the junction with the additive introduction point 144, or downstream of the additive introduction point.

To analyze the composition or characteristics of the reverse osmosis water flow after mixing with the additive, the dialysate system 120 can include a first sensor 150 downstream of and in fluid communication with the mixing chamber 146. In the illustrated embodiment, the first sensor 150 can be a conductivity sensor that measures the electrical conductivity of the reverse osmosis water flow. For example, liquid may have the ability to conduct or pass an electrical current. The electrical charge is carried by electrolytes or ions, including cations (positive) and anions (negative), present in the fluid. The number of ions in the fluid, and thus the ability of the fluid to conduct or resist electric current, is dependent upon a number of factors including the composition of the fluid, temperature, flow rate and volume. If factors such as volume and temperature are known and accounted for, then the measurable conductivity of the fluid can be used to deduce the unknown composition of the fluid.

To measure the conductivity of a fluid, the conductivity sensor is configured to apply a current or voltage to a volume of the fluid between two predetermined points or locations. The resistivity of the fluid to passing electricity, which is the mathematic reciprocal of conductivity, causes a drop or decrease in the voltage and/or current between the two points. An appropriate electrical meter can measure the decrease in those parameters which are reflective of the fluid's resistivity and thereby establish the conductivity of the fluid by the mathematic relation. The physical and electrical coupling between the conductivity sensor and the fluid occurs in a conductivity cell that includes electrodes to apply and sense the voltage and/or current.

Various types of conductivity cells exist for use in conductivity sensors. For example, in the embodiment of FIG. 2, a three-electrode conductivity cell 152 is depicted. The three-electrode conductivity cell 152 is configured as a flow-through device and includes a hollow, cylindrical tube 154 of known dimensions, including diameter and length, disposed in-line with the tubing 134. Because the dimensions of the cell are fixed, the cell can receive a known or predetermined volume or flow rate of fluid. This relationship may be used to establish a cell constant that can be later used in calculating the conductivity of the fluid in the cell. Disposed radially around the tube 154 can be a plurality of torus or ring-shaped, conductive electrodes 156, 158 that are axially spaced-apart from each other. The axially outward two electrodes 156 can be designated excitation electrodes communicating with a voltage or current generator 160, and the center electrode 158 can be designated a sense electrode communicating with an appropriate meter 162. When a voltage or current is applied between the excitation electrodes 156 causing current to flow in the fluid, the center electrode 158 can directly sense the charge drop along the axis of the tube 154. The conductivity is thereby determined and can be used to assess the composition of the reverse osmosis water flow including the additive inside the conductivity cell 152.

In an alternative embodiment of the three-electrode cell, the center electrode 158 can be the excitation electrode and the outer electrodes 156 can be the sense electrodes. Another known type of conductivity cell is the two-electrode cell that includes one excitation electrode and one sense electrode. Another type is the four-cell electrode that includes two axially-spaced excitation electrodes and two inwardly disposed sense electrodes that sense the charge drop between the outer excitation electrodes. The electrodes can be in direct or indirect contact with the fluid in any of the foregoing cells.

In other embodiments, different styles or designs of sensors can be employed to determine the composition of the reverse osmosis water flow. For example, an ion selective electrode (ISE) sensor can be used to measure the ion concentration of a specific type of ion in the water flow. The ISE can include a reference electrode separated from the solution by an ion-specific membrane that is permeable to specific ions. When a specific type of ion interacts with the ISE, the electrode converts the interaction into an electrical potential or an electrical charge that can be detected by an appropriate meter. Other kinds of suitable sensors can include pH sensors, micro electrical-mechanical system (MEMS) sensors, and other sensors that measure different electrical or physical characteristics of the reverse osmosis water.

The dialysate system 120 can introduce additional additives to the reverse osmosis water flow to further adjust the dialysate. For example, to adjust the acidity of the solution which affects the acidity of the blood returned to the patient, an acid source 170 containing an acid such as acetate can be in fluid communication with the tubing 134 downstream of the first sensor 150. The introduction point of the acid source 170 can be a second mixing chamber 172 to mix the reverse osmosis water flow with the acid. To produce highly pure or ultrapure reverse osmosis water, the dialysate system 120 can include additional dialysate filters communicating with the dialysate line. To accurately control the quantity of the reverse osmosis water flow delivered to the dialyzer 110, the dialysate system 120 can include a balancing chamber 174 disposed in-line with the tubing 134. The balancing chamber 174 can function to accurately regulate and adjust the quantity of reverse osmosis water delivered based on the treatment conditions and can function as a reservoir to facilitate thorough mixing of the additives and reverse osmosis water prior to directing the mixture to the dialyzer 110. A second sensor 176 can be disposed downstream of the balancing chamber 174 and upstream of the dialyzer 110 to measure, for example, the final composition, temperature or flow rate of the dialysate exiting the dialysis machine 100 through the exit port 178.

After the dialysate passes through the dialyzer 110 and interfaces with the blood, the spent dialysate can be directed to a waste reservoir 180 associated with the dialysis machine 100 for later disposal. This is facilitated by a waste line 182 fluidly communicating between the waste reservoir 180 and the dialyzer 110. In an embodiment, the waste line 182 can be directed through the balancing chamber 174 to help maintain an equilibrium of dialysate flow and/or volume by regulating the quantity of dialysate into and out of the dialyzer 110.

To monitor and control the dialysate formation process, an electronic or computerized control unit, module or controller 190 can be associated with the dialysis machine 100. The controller 190 is adapted to monitor various operating parameters and to responsively regulate various variables and functions affecting the dialysate system 120 and the other systems of the dialysis machine 110. The controller 190 can include a microprocessor, an application specific integrated circuit (ASIC), or other appropriate circuitry, and can have memory or other data storage capabilities. Furthermore, the controller 190 can include or be operatively associated with the display screen 126 and the control panel 128 described above to interface with the technician.

Communication between the controller and the system can be established by sending and receiving digital or analog signals across electronic communication lines or communication busses, indicated in dashed lines for illustration purposes. For example, to control and adjust the amount of additive introduced to the reverse osmosis water flow, the controller 190 can electronically communicate with the additive pump 142. To determine the composition of the mixture of reverse osmosis water and additive, the controller 190 can electronically communicate with the first sensor 150 downstream of the additive introduction point 144. The controller 190 can include logic or computer executable instructions to convert or translate signals from the first sensor 150 into the conductivity or another electrical or physical characteristic of the solution therein and to determine fluid composition from the measured conductivity or characteristic. Thus, based on the conductivity of the reverse osmosis water flow through the first sensor 150, the controller 190 can adjust the composition by, for example, selectively activating and deactivating the additive pump 142 with which the controller also electronically communicates.

In addition to sensing the conductivity or another characteristic of the reverse osmosis water flow mixed with the introduced additive, the first sensor 150 can also measure conductivity or another characteristic of the unmixed reverse osmosis water due to its location in the dialysate system 120. Specifically, because the first sensor 150 is disposed downstream of the additive introduction point 144, the first sensor receives the combined streams of the reverse osmosis water flow from the reverse osmosis water source 130 and the bicarbonate solution from the additive source 140. Accordingly, at times when the additive pump 142 is inactive and additive is not introduced to the mixing chamber 146, the first sensor 150 will be receiving substantially pure reverse osmosis water flow. Measurements from the first sensor 150 during these times will reflect the conductivity of pure reverse osmosis water, which should approach the conductivity of pure, de-ionized water that is very low, approaching zero. This is in contrast to conductivity measurements of the reverse osmosis water/additive mixture that may be substantially higher due to electrolytes and ions present in the additives. In other embodiments, different types of sensors can measure similar electrical or physical characteristics of the reverses osmosis water flow.

Figure 3:
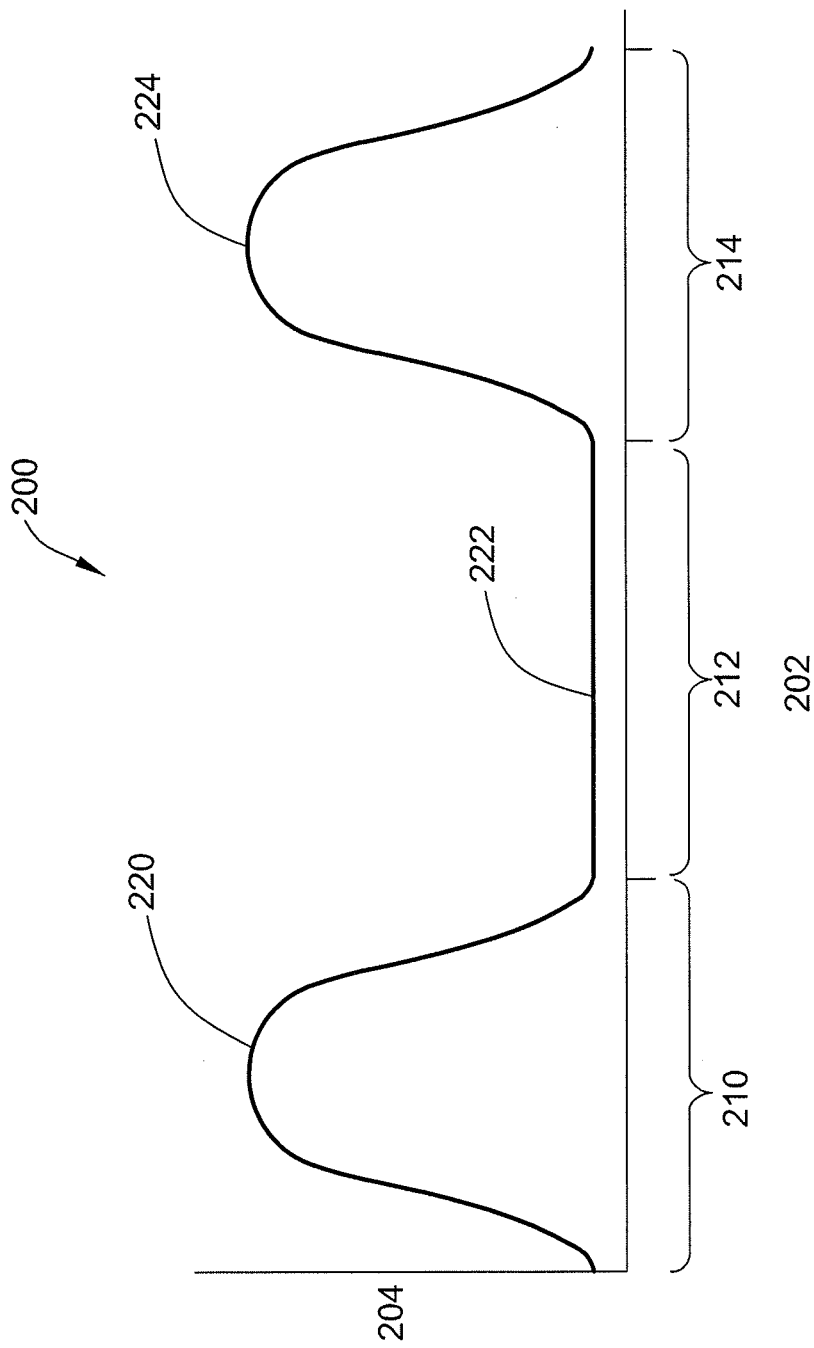
FIG. 3 is a chart representing the cyclic measurements of the conductivity of the dialysate during the course of intermittent and/or sequential introduction of an additive to the reverse osmosis water flow, with conductivity plotted on the Y-axis and time plotted on the X-axis.

FIG. 3 depicts a chart illustrating the conductivity measurements from the first sensor at times when additive is introduced to the reverse osmosis water flow and at times when it is not. The chart 200 represents or measures time along the X-axis 202 and conductivity along the Y-axis 204. Time can be measured in seconds and conductivity in Siemens or micro Siemens. During an initial or first time period 210 when the additive pump is actively introducing additive to the reverse osmosis water stream, the first sensor will measure an increased or heightened conductivity level as indicated by the first bell-shaped curve 220. During a second time period 212 when the additive pump ceases activity and the first sensor receives substantially pure water, the measured conductivity decreases to the low, flat curve 222. During a third time period 214, the additive pump can recommence activity introducing additive and the first sensor measures a corresponding increase in conductivity represented by the second bell curve 224. The process of alternating active and inactive periods of the additive pump can be referred to as dosing or pulsing. The upward and downward slopes of the first and second bell curves 220, 224 reflect that the changes in additive concentration of the reverse osmosis water entering the first sensor may be relatively gradual rather than suddenly abrupt.

Figure 4:
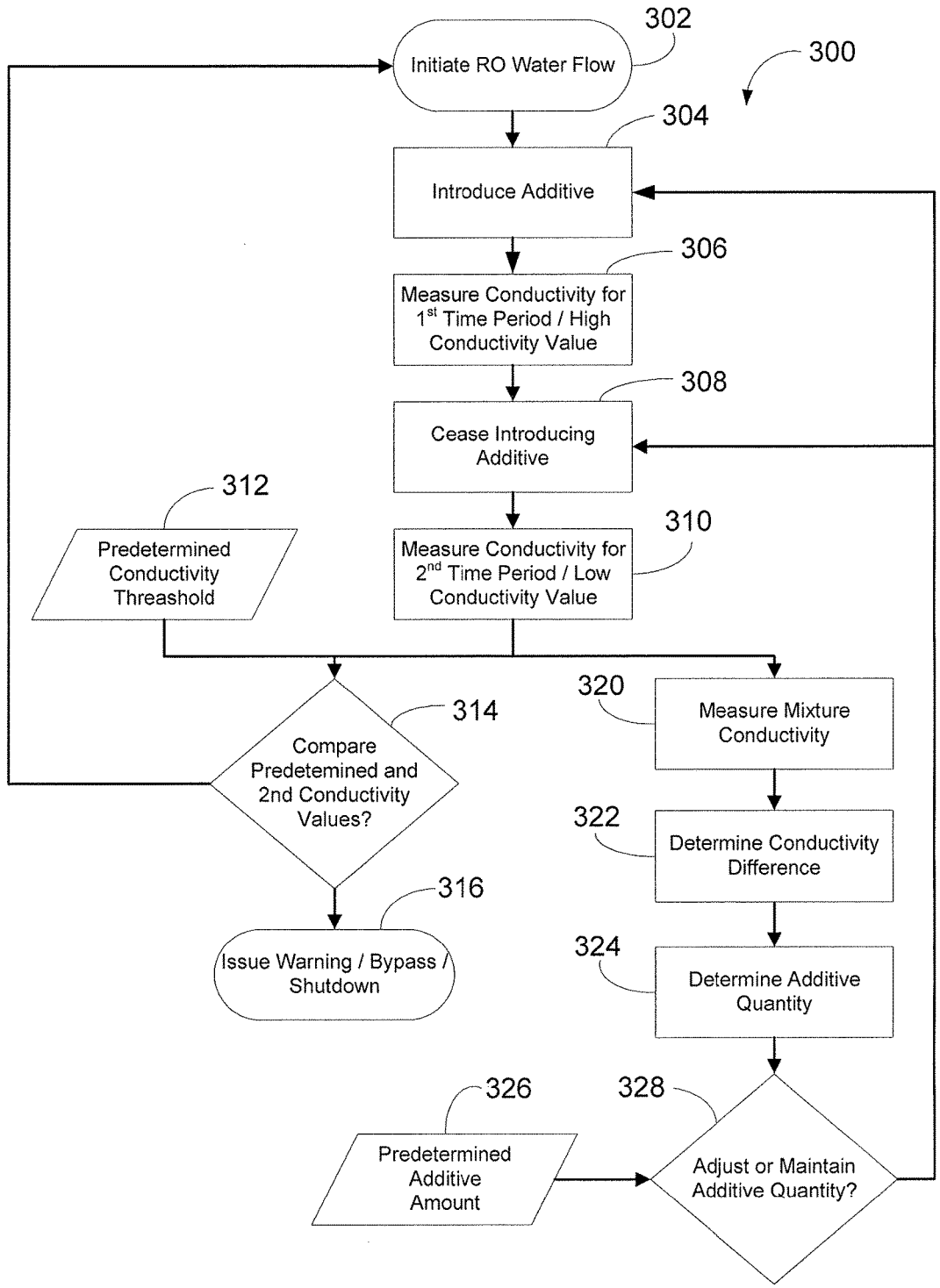
FIG. 4 is a flowchart representing possible steps or routines for measuring the conductivity of the dialysate and responsively controlling the dialysis machine and treatment.

The controller can utilize information regarding the changes in conductivity or another characteristic measured by the first sensor to control and adjust operation of the dialysis machine and relatedly the dialysis treatment. For example, referring to FIG. 4, there is illustrated a flowchart 300 of possible routines, processes or strategies the controller can perform and can include logic or executable software instructions to implement utilizing the conductivity information or similar information regarding other electrical or physical characteristics received from the first sensor. With reference to FIGS. 2, 3, and 4, in an initial flow step 302, the controller 190 can command the reverse osmosis water source 130 to begin introducing reverse osmosis water to the dialysis machine 100. In an additive introduction step 304, the controller 190 can activate the additive pump 140 to introduce additive to the mixing chamber 146 which mixes with the primary reverse osmosis water flow. The first sensor 150 receives the mixture and registers a relatively high conductivity value that is communicated to and processed by the controller 190 during a first measurement step 310.

In an embodiment, the additive pump 142 may be active for a predetermined first time period 220 such that the first measurement step 306 measures high conductivity or a similar characteristic for a fixed time. The predetermined first time period 220 may be established by the controller 190 or by another component of the dialysis machine 100. In another embodiment, the additive pump may be manually controlled by a technician. In such instances, the controller 190 in the first measurement step 306 may recognize and register a non-temporal high conductivity value. At a certain instance, in a cease additive step 308, the additive pump 142 may cease introducing bicarbonate to the reverse osmosis water flow. The cease additive step 308 may be commanded at a predetermined time or under predetermined conditions by the controller 190 or may be initiated manually by a technician. Accordingly, in a second measuring step 310 subsequent to the cease additive step 308, the controller 190 measures relatively low conductivity or a comparable change in value for another characteristic such as electrical potential or charge. These conditions may occur for the predetermined second time period 222. Alternatively, the controller 190 may perceive the result of the second measurement step 310 as a non-temporal low conductivity value. The low conductivity value is reflective of the conductivity and thus the composition of the reverse osmosis water flow less any additive, i.e., purified reverse osmosis water.

The controller 190 can include programmable instructions to process the information determined by the first and second measurement steps 306, 310 for assisting control and operation of the dialysis machine 100. For example, the controller 190 can be programmed with or otherwise receive a predetermined conductivity threshold 312 representing a maximum acceptable conductivity level of the revere osmosis water flow. In a first comparison step 314, the controller can compare the predetermined conductivity threshold 312 with the low conductivity value measured in the second measurement step 310. If the measured low conductivity value exceeds the predetermined conductivity threshold 312, that can indicate to the controller 190 that the reverse osmosis water is unacceptably contaminated. If the first comparison step 314 results in an unacceptability determination, the controller 190 can initiate an appropriate, protective step 316 to avoid the unacceptable water from interfacing with blood in the dialyzer 110. For example, the protective step 316 can involve issuing a warning via warning lights or audio alarms to the technician through the display device 126. Additionally, the protective step 316 can redirect the reverse osmosis water flow to bypass the dialyzer, or the protective step 316 can shutdown operation of the dialysate system 120.

In an alternative process, the controller 190 can include executable instructions to determine the quantity of additive introduced to the reverse osmosis water from the measured conductivity values. For example, the controller in a mixture measurement step 320 can determine the conductivity of the mixture of reverse osmosis water and additive. The mixture measurement step 320 can be performed using values from the first measurement step 306, or by performing a third measurement step using the downstream second sensor 176. In a difference determination step 322, the controller 190 can determine the difference between the mixture conductivity value and the low conductivity value measured by the second measurement step 310. The mixture conductivity value associated with pure reverse osmosis water is presumably higher than the low conductivity value associated with pure reverse osmosis water.

The difference between the mixture and low conductivity values can qualitatively correspond to the quantity of additive of a known composition introduced to the pure reverse osmosis water flow. The correspondence between conductivity and quantity of additive can be determined empirically, for example. Accordingly, in a quantity determination step 324, the quantity of additive added can be determined as, for example, a volumetric basis. In a second comparison step, the additive quantity can be compared to a predetermined amount of additive 326 as, for example, directed by the dialysis treatment. The result of the second comparison step 328 can cause the controller to direct adjustment of the additive quantity by, for example, returning to the additive introduction step 304 or the cease introduction step 308. In an aspect, the quantity determination step 324 can be applied in conjunction with the regulation of additive performed by the additive pump 142 as, for example, a system check or calibration assessment. For example, if the quantity of additive measured does not equal the quantity of the additive intended for introduction, or more directly if the first sensor 150 measures aberrant or abnormal conductivity values during the respective first and second time periods, the controller 190 may determine that the additive pump 142 is leaking or failing and take appropriate action.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of measuring dialysate characteristics in a dialysis system comprising:
   receiving a substantially pure water flow upstream of a mixing chamber;
   diverting a portion of the substantially pure water flow through a diverting branch having an additive source to form an additive solution;
   mixing the additive solution with the undiverted substantially pure water flow the mixing chamber to form fresh dialysate;
   measuring an electrical characteristic of the additive in the fresh dialysate during a first time period using a sensor downstream of the mixing chamber and upstream of an exit port of the dialysis system configured to communicate with a dialyzer;
   ceasing introduction of the additive to the diverted portion during a second time period; and
   measuring the electrical characteristic of the pure water flow during the second time period using the sensor.

2. The method of claim 1, further comprising comparing the electrical characteristic of the substantially pure water flow to a predetermined threshold.

3. The method of claim 2, wherein the sensor is a conductivity cell and the electrical characteristic is conductivity.

4. The method of claim 3, further comprising:
   measuring a conductivity of a mixture of the additive and the substantially pure water flow;
   comparing the conductivity of the mixture with the conductivity of the substantially pure water flow; and
   determining a quantity of the additive introduced to the substantially pure water flow.

5. The method of claim 3, wherein the conductivity cell is selected from the group consisting of a two-electrode cell, a three-electrode cell, and a four-electrode cell.

6. The method of claim 1, wherein the additive is bicarbonate or a bicarbonate solution.

7. The method of claim 1, further comprising introducing a second additive to the fresh dialysate at a second additive source disposed downstream of the sensor and upstream of the exit port of the dialysis system.

8. A dialysis machine comprising:
   a substantially pure water introduction port for receiving a substantially pure water flow from a substantially pure water source;
   an additive source for supplying an additive to form an additive solution;
   a diverting branch for diverting a portion of the substantially pure water flow to the additive source;
   an additive introduction point downstream of the substantially pure water introduction port and fluidly communicating with the additive source;
   a mixing chamber proximate the additive introduction pint for mixing the additive solution and the undiverted substantially pure water flow;
   a sensor downstream of the mixing chamber and upstream of an exit port of the dialysis machine configured to communicate with a dialyzer; and
   a controller electrically communicating with the sensor and including executable instructions to measure an electrical characteristic during a first time period using the sensor when the additive solution is introduced to the substantially pure water flow and to measure the electrical characteristic during a second time period using the sensor when the additive solution is not introduced to the substantially pure water flow.

9. The dialysis machine of claim 8, wherein the sensor is a conductivity cell and the electrical characteristic is conductivity.

10. The dialysis machine of claim 9, wherein the conductivity cell is selected from the group consisting of a two-electrode cell, a three-electrode cell, and a four-electrode cell.

11. The dialysis machine of claim 10, further comprising an additive pump fluidly communicating with the additive source and the additive introduction point.

12. The dialysis machine of claim 11, wherein the additive pump is in electronic communication with the controller and the controller further includes executable instructions to intermittently and selectively activate the additive pump to introduce the additive to the substantially pure water flow through the additive introduction point.

13. The dialysis machine of claim 12, wherein the controller further includes executable instructions to compare conductivity during the second time period with a predetermined threshold.

14. The dialysis machine of claim 13, wherein the controller further includes an executable instruction to compare conductivity during the second time period with conductivity of a mixture of the additive solution and the substantially pure water flow and to compare conductivity of the substantially pure water with a conductivity of the mixture.

15. The dialysis machine of claim 14, wherein the controller further determines a quantity of the additive introduced into the substantially pure water flow.

16. The dialysis machine of claim 8, wherein the additive in the additive source is bicarbonate or a bicarbonate solution.

17. A method of controlling a dialysis machine comprising:
   directing a substantially pure water flow through the dialysis machine;
   selectively diverting a portion of the substantially pure water flow through a diverting branch to an additive source to prepare an additive solution;
   intermittently introducing the additive solution to the substantially pure water flow in a mixing chamber and mixing with undiverted substantially pure water flow to prepare fresh dialysate;
   measuring a conductivity of the substantially pure water flow with a sensor in fluid communication with the mixing chamber and with an exit port of the dialysis machine configured to communicate with a dialyzer; and
   determining a high conductivity value at a first time period and a low conductivity value at a second time period for the substantially pure water flow, wherein the low conductivity value corresponds to the conductivity of the substantially pure water flow absent or substantially absent the additive.

18. The method of claim 17, further comprising comparing the low conductivity value with a predetermined threshold.

19. The method of claim 17, further comprising:
   measuring a mixture conductivity value of a mixture of the additive and the substantially pure water flow;
   comparing the mixture conductivity value with the low conductivity value; and
   determining a quantity of the additive introduced into to the substantially pure water flow.

20. The method of claim 17, wherein the additive is bicarbonate.

* * * * *

UNITED STATES PATENT AND TRADEMARK OFFICE
CERTIFICATE OF CORRECTION

PATENT NO. : 9,731,059 B2  
APPLICATION NO. : 13/933828  
DATED : August 15, 2017  
INVENTOR(S) : Crnkovich et al.

Page 1 of 1

It is certified that error appears in the above-identified patent and that said Letters Patent is hereby corrected as shown below:

In the Claims

Claim 1, Column 9, Line 51:
"flow the mixing chamber" should read --flow in the mixing chamber--

Signed and Sealed this
Tenth Day of August, 2021

Drew Hirshfeld
*Performing the Functions and Duties of the*
*Under Secretary of Commerce for Intellectual Property and*
*Director of the United States Patent and Trademark Office*